(12) United States Patent
McHugh (10) Patent No.: US 6,230,047 B1
(45) Date of Patent: May 8, 2001

(54) MUSICAL LISTENING APPARATUS WITH PULSE-TRIGGERED RHYTHM

(76) Inventor: David McHugh, 71 Robinhood Cir., Winston-Salem, NC (US) 27106

( * ) Notice: Subject to any disclaimer, the term of this patent is extended or adjusted under 35 U.S.C. 154(b) by 0 days.

(21) Appl. No.: 09/419,257

(22) Filed: Oct. 15, 1999

Related U.S. Application Data

(60) Provisional application No. 60/104,398, filed on Oct. 15, 1998.

(51) Int. Cl.[7] ........................................................ A61B 5/02
(52) U.S. Cl. ............................................................ 600/519
(58) Field of Search ..................................... 600/502, 503, 600/509, 508, 519, 520

(56) References Cited

U.S. PATENT DOCUMENTS 4,788,983 * 12/1988 Brink et al. .

* cited by examiner

*Primary Examiner*—Scott M. Getzow
(74) *Attorney, Agent, or Firm*—Charles W. Calkins; Kirkpatrick Stockton LLP

(57) ABSTRACT

An apparatus combines a plurality of incoming audio signals and outputs a combined audio signal. The incoming audio signals include a music signal, e.g., from a CD or cassette player, and a rhythm signal triggered by a user's heartbeat. The tempo of the rhythm will increase or decrease with the pulse rate of the user. In an alternative embodiment, the tempo may be set at a predetermined level to raise or lower the heartbeat of the user.

The apparatus includes means for storing a plurality rhythm patterns on memory means, means for the user to select one of the rhythm patterns, means for outputting the selected rhythm pattern to create a rhythm signal, means for receiving a pulse signal corresponding to the user's pulse, means for combining the rhythm signal and the pulse signal to create a linked rhythm/pulse signal, means for receiving an audio signal from a music playback device, a musical mixing device to combine the linked rhythm/pulse signal and the audio signal to create a combined rhythm/pulse/audio signal, and means for outputting the combined rhythm/pulse/audio signal.

Also disclosed is a musical listening system which includes the musical listening apparatus of the present invention and further comprises means for monitoring a user's pulse to generate the pulse signal, a musical playback device to generate the audio signal, and means for receiving and outputting the combined rhythm/pulse/audio signal.

16 Claims, 7 Drawing Sheets

MUSICAL LISTENING APPARATUS WITH PULSE-TRIGGERED RHYTHM

CROSS-REFERENCE TO RELATED APPLICATIONS

This application claims the benefit of U.S. Provisional Application No. 60/104,398, filed Oct. 15, 1998.

FIELD OF THE INVENTION

The present invention relates to apparatus, systems and methods that link an audio signal and an individual's pulse rate (heartbeat), musical listening devices which include the apparatus and/or systems, and methods for listening to music utilizing the apparatus and/or systems.

BACKGROUND

Listening to music while performing physical exercise is very popular. Often a person exercising will listen to music from a compact disc, SONY MINIDISC™, a tape (e.g., a cassette, 8-track, or reel-to-reel tape) or a record (e.g., LP). The music may be played through audio speakers in the room where the person is exercising or audio speakers attached to headphones worn by the exerciser.

A problem of listening to music while exercising is that the music often has a steady tempo which is not in sync with the tempo of the person exercising, as reflected by the person's pulse rate. Accordingly, it would be advantageous to have an apparatus for combining an audio signal received from a music playback device with a signal received from a person's pulse rate and a rhythm signal from a rhythm track to produce a combined audio signal which is linked to a person's pulse rate.

Another problem which afflicts many people in society is anxiety attacks, or other emotional or physical disturbances which cause the individual's heartbeat to rise, and the person's heart to beat rapidly. It would be advantageous to have a device that would have a calming effect to relieve the person's anxiety while also slowing their heartbeat.

SUMMARY OF THE INVENTION

The present invention provides apparatus, systems and methods for providing audio that is correllated to an individual's heart rate. The audio comprises a rhythm that is played at a selected tempo corresponding to an individual's heart rate. The rhythm may comprise an instrumental track produced by percussion, bass or other instruments. The audio may further comprise music, including but not limited to orchestral, new wave, alternative, jazz, vocal, rock, punk, bebop, pop, swing, soul, country, folk and/or other forms of music. The tempo of the music may be correllated to the rhythm tempo, or may be at a different tempo. When the audio comprises music, the rhythm track may form part of the music.

In a first aspect, the present invention provides a system comprising:

a memory or storage device including stored rhythm patterns;

a selector including a plurality of locations, each location corresponding to a stored rhythm pattern;

a signal generator capable of producing a rhythm signal corresponding to a selected rhythm pattern;

a pulse reader capable of obtaining an individual's pulse rate;

a pulse signal generator capable of producing a pulse signal corresponding to the user's pulse rate;

one or more transmission media capable of transmitting the pulse signal and rhythm signal;

a mixer for receiving the rhythm signal and pulse signal and capable of linking the signals to produce an combined signal;

at least one transmission medium capable of transmitting the combined signal; and at least one speaker for playing the combined signal.

A system of the present invention may further comprise a musical playback device such as a MP3 player, cd player, tape player, record player, radio or the like that generates an audio signal; and one or more transmission media capable of transmitting the audio signal to the mixer wherein the audio signal is combined with the pulse and rhythm signals in the mixer to produce a single combined signal for the speaker.

Suitable memory or storage devices include electronic memory devices such as DRAM's, RAM, ROM's and other conventional memory devices.

Suitable selectors include mechanical switches, such as toggle, slide, detent or rotary switches and/or electronic switches such as touch sensitive switches or pads.

Suitable pulse readers for use in the present invention include conventional apparatus for measuring heart rate, including conventional pulse monitors such as the type marketed by POLAR electronics.

Suitable transmission media include wires, infrared or radio frequency transmitters. In the following description wires are referenced as the transmission media however other media may be substituted.

Suitable signal generators include those of the type conventionally utilized in music playback devices and other hand held electronic equipment.

Suitable mixers include those known to ordinary skill in the art.

Suitable speakers include headphones, in the ear speakers, loudspeakers and the like.

According to another aspect of the present invention, a method for collating an audio signal and an individual's heart rate comprises:

obtaining a pulse based signal corresponding to an individual's heart rate;

transmitting the pulse based signal to a mixer;

transmitting a rhythm signal corresponding to a desired rhythm pattern to the mixer;

mixing the pulse based signal and the rhythm signal to produce a combined signal. Other methods of the present invention may further include transmitting the combined signal to a speaker for playback to an individual. In addition, an audio signal may be obtained from a musical playback device and also combined with the pulse aid rhythm signals.

In another aspect, the present invention provides an apparatus which receives a signal from the heartbeat of an individual user and triggers a programmed rhythm that is played at the tempo of the user's heartbeat. As the user's pulse rate increases, the tempo of the rhythm correspondingly increases; as the user's pulse rate decreases, a corresponding decrease also occurs. The apparatus advantageously correlates the musical rhythm that is heard with the rate of the individual's heartbeat and allows a user to exercise to his/her own internal clock.

In a further aspect, the present invention provides an apparatus which may be utilized to slow a person's heartbeat via a programmed rhythm that is played at a desired, e.g. normal, heartbeat while receiving a signal from the heartbeat of the user. The programmed rhythm is played at least as long as the person's heartbeat is above the desired heartbeat. At the point the heartbeat signal indicates the desired heartbeat is reached, the programmed rhythm may continue, or may halt. Alternatively, an audio signal may be triggered to indicate to the user that the desired heartrate has been reached.

In a still further aspect, the present invention provides an apparatus which may be utilized to raise a person's heartbeat to a desired, or preprogrammed level, to permit the person to exercise at that level. This aspect is similar to the aspect discussed above, except that the programmed rhythm is played a level above the person's resting heartbeat.

An apparatus of the present invention may comprise:

means for storing a plurality of rhythm patterns on memory means such as a chip;

means for the user to select one of the rhythm patterns for output;

means for outputting the selected rhythm pattern to create a rhythm signal;

means for receiving a pulse signal corresponding to a user's pulse rate;

means for combining the rhythm signal and the pulse signal to create a linked rhythm/pulse signal;

means for receiving an audio signal from a music playback device such as a portable CD or cassette player or a music chip;

musical mixing means for combining the linked rhythm/pulse signal and the audio signal to create a combined rhythm/pulse/audio signal and:

means for outputting the combined rhythm/pulse/audio signal.

The apparatus may further comprise one or more of the following features:

means for outputting the pulse signal to the user, means for correlating the pulse signal to a predetermined heartbeat chosen by the user;

user programmable means for generating a pulse alarm signal corresponding to a user defined pulse rate and means for outputting the alarm signal to the user; and electrical communication means (e.g. wires or wireless) for communicating the signals between said means.

A musical playback system of the present invention comprises an apparatus of the present invention and further comprises means for monitoring a user's pulse to generate the pulse signal (e.g., a pulse monitor), a musical playback device to generate the audio signal, and means for receiving and outputting the combined rhythm/pulse/audio signal, for example, audio speakers or headphones.

The beating of the heart indicates the degree to which a person is at rest or stimulated. In an age when we are viewing life in increasingly holistic terms, the apparatus and/or system of the present invention advantageously allows an individual to exercise to the beating of their own heart, and to change the tempo of their workout as the pulse rate changes. The individual may put theirself in their own rhythm loop.

In accordance with another feature of the apparatus of the present invention the apparatus also advantageously provides a user with means for continuously monitoring their pulse rate.

An apparatus is disclosed for linking a rhythm track with a heartbeat of a user. The apparatus includes a pulse monitor, a processor, and an output device. The pulse monitor produces a pulse signal corresponding to the heartbeat of the user. The processor includes memory for storing at least one rhythm pattern data. The processor receives the pulse signal and the rhythm pattern data, and the processor links the pulse signal with the rhythm pattern data to produce an output signal. The output device receives the output signal from the processor. The apparatus may further include a switch to allow the user to select a desired rhythm pattern data, and processor receives the selected rhythm pattern data.

BRIEF DESCRIPTION OF THE SEVERAL VIEWS OF THE DRAWINGS

Further features and advantages of the apparatus and system of the present invention will become apparent from the following more detailed description and from the appended figures, wherein.

DETAILED DESCRIPTION OF THE INVENTION

Figure 1:
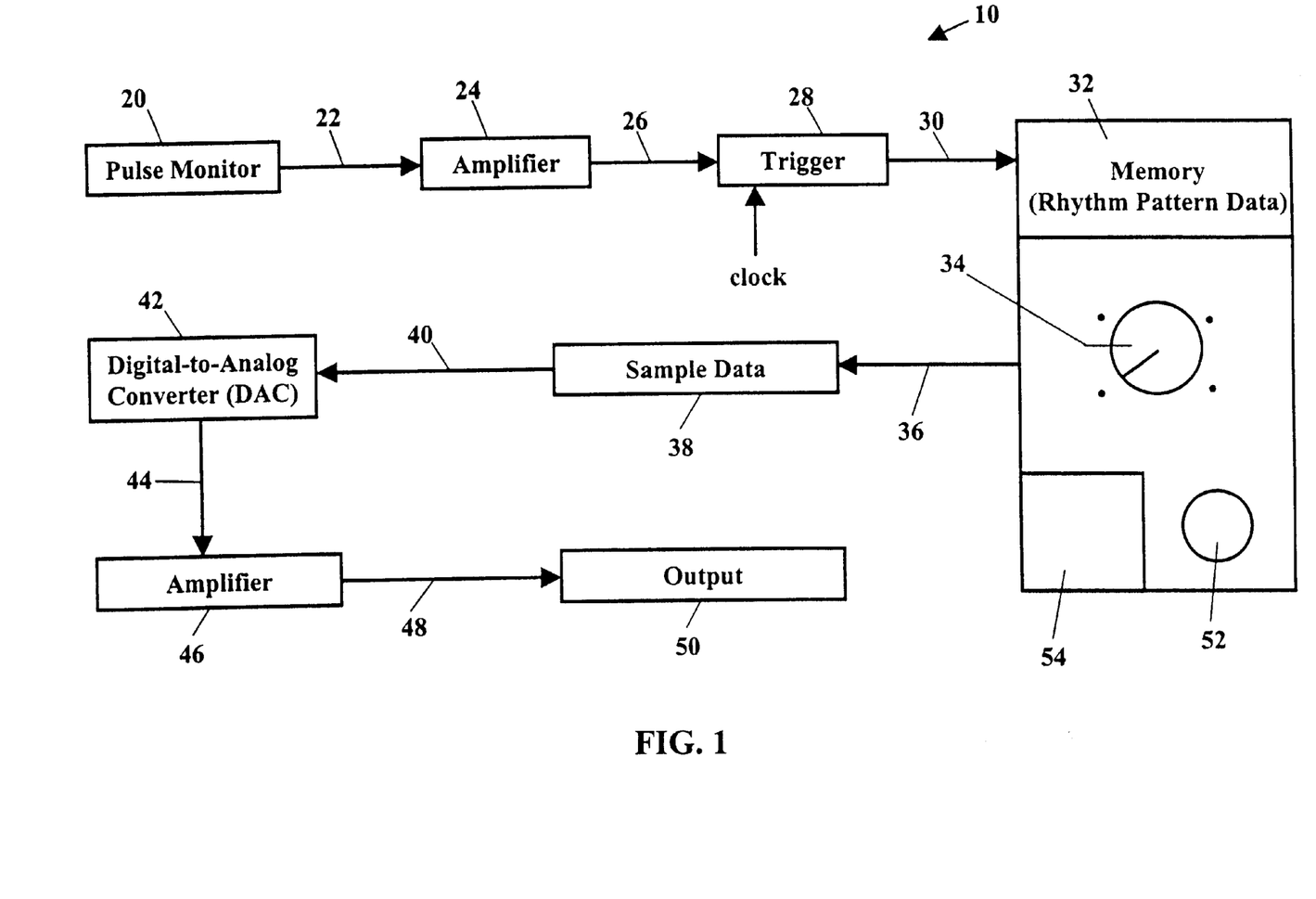
FIG. 1 is a schematic diagram and flowchart of an embodiment of an apparatus of the present invention.

FIG. 1 is a schematic diagram and flow chart of an embodiment of an apparatus 10 of the present invention. An embodiment of the present invention includes means 20 for monitoring a user's pulse and for generating an output pulse signal 22. The output pulse signal 22 corresponds to the user's heart rate (e.g., pulse). The means 20 for monitoring a user's pulse may comprise a conventional electromagnetic sensor, such as an infrared or photoelectric pulse sensor. The means for monitoring a user's pulse may alternatively comprise a conventional pressure sensor or other pulse sensor that is conventionally known in the art. The means 20 for monitoring a user's pulse preferably comprises an ear lobe clip. Such ear lobe sensors may be clipped to the user's ear lobe to detect a pulse rate. Although an ear lobe sensor is preferred, those skilled and unskilled in the art recognize a user's pulse may alternatively be monitored at the wrist, neck, finger, chest, or any other suitable location.

The output pulse signal 22 is received by first amplifying means 24. The first amplifying means 24 adds gain to the output pulse signal 22 to produce an amplified pulse signal 26. The first amplifying means 24 may comprise an operational amplifier as is conventionally known.

The amplified pulse signal 26 is received by trigger means 28. The trigger means 28 may utilize a conventional Musical Instrument Digital Interface (MIDI) means. The trigger means 28 receives a clock input and provides a trigger signal 30. The trigger signal 30 is communicated to means 32 for storing rhythm pattern data. The means 32 for storing rhythm pattern data preferably comprises a processor chip with memory. The chip has been preprogrammed with a plurality of rhythm pattern data, and the chip generates rhythm tracks from the plurality of rhythm pattern data. The rhythm pattern data may include, for example, rhythm tracks that simulate percussion instruments, bass instruments, or any other instruments or combination of instruments that are useful in providing a beat or rhythm. The means 32 for storing rhythm pattern data may also communicate with means 34 for selecting. The means 34 for selecting allows the user to select from the preprogrammed rhythm pattern data. The means 34 for selecting preferably includes a multi-position rotary, toggle, touch pad, slide switch or similar device that allows the user to select a desired rhythm. The means 34 for selecting may even include a sequential light to indicate each rhythm pattern.

The means 32 for storing rhythm pattern data produces an output signal 36. The output signal 36 comprises sampled trigger commands. As those skilled in the art recognize, the chip receives the pulse signal and the rhythm pattern data, and the chip combines the pulse signal and the rhythm pattern data. The output signal 36 represents a linked rhythm and pulse output signal.

The output signal 36 is received by sampling means 38. Sampling means 38 produces a digital audio sample information signal 40. The digital audio sample information signal represents a linked rhythm and pulse output signal. This digital audio sample information signal is received by a Digital-to-Analog Converter (DAC) 42. The Digital-to-Analog Converter (DAC) 42 receives a digital signal and, as is conventionally known, converts the digital signal into an analog signal 44. The analog signal 44 is received by a second amplifying means 46. The second amplifying means 46 adds gain to the analog signal 44 to produce an amplified analog signal 48. The second amplifying means 46 may comprise an operational amplifier as is conventionally known.

The amplified analog signal 48 is received by an output device 50. The output device 50 may be audio speakers, such as conventional stereo headphones of the type utilized with portable music playing devices. The amplified analog signal 48, in this embodiment, is a triggered, programmed rhythm that is played at the tempo of the user's heart rate. As the user's pulse rate increases, the tempo of the rhythm correspondingly increases; as the user's pulse rate decreases, the tempo of the rhythm correspondingly decreases. The system advantageously correlates the heartbeat pace of the user with the musical rhythm that is heard and allows the user to exercise to the user's own internal clock.

The apparatus 10 of the present invention may further comprise means for outputting the pulse rate signal 22 to the output device 50. The user could press a button 52, for example, and the processor chip would announce the user's pulse rate to the output device 50. The user could press the button and hear, through the headphone speakers, the user's own pulse rate. The system 10 of the present invention may alternatively, or additionally, further comprise means for alerting the user. The means for alerting the user is shown as alarm circuitry 54. The user could set an alarm to a desired pulse rate. The alarm circuitry receives the pulse rate signal 22 and alerts the user when the desired pulse rate is achieved and/or exceeded.

Another aspect of the present invention may also be utilized to slow the user's heartbeat. A programmed rhythm is played at a desired, e.g., normal, heartbeat. The programmed rhythm is played at least as long as the user's heartbeat is above the desired heartbeat. At the point the heartbeat signal 22 indicates the desired heartbeat is reached, the programmed rhythm may continue or may halt.

Still another aspect of the present invention may be utilized to raise a user's heartbeat. A programmed rhythm is played at a desired, or preprogrammed level, to permit the user to exercise at that level. This aspect is similar to the aspect discussed above, except that the programmed rhythm is played at a level above the person's resting heartbeat.

The apparatus of the present invention is preferably portable to permit the apparatus to be worn while the user is running, jogging, riding a bicycle, or performing any other physical activity. An apparatus of the present invention may also be constructed to be non-portable for use in an exercise room or a similar setting.

Figure 2:
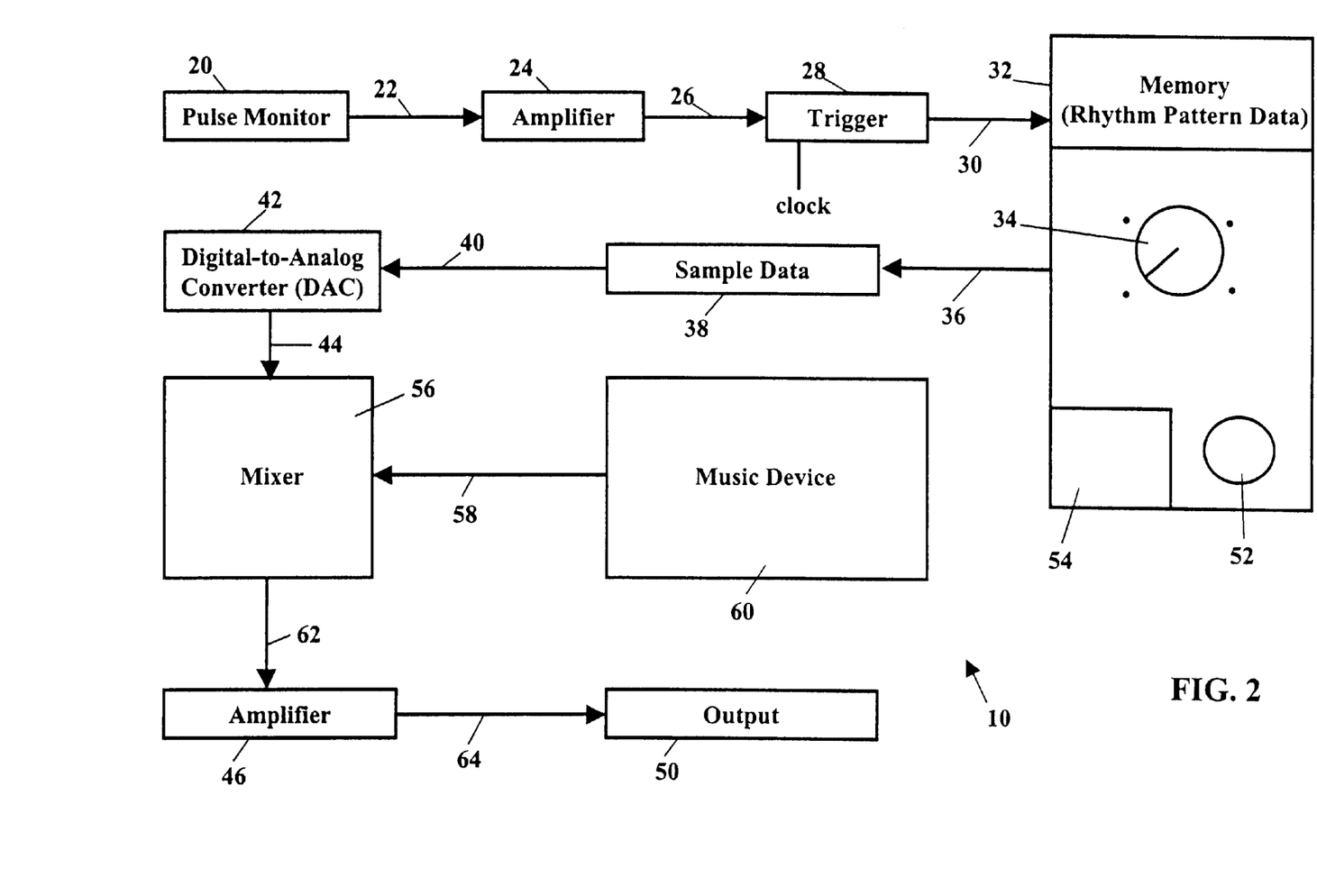
FIG. 2 is a schematic diagram and flowchart of an alternative embodiment of the present invention.

FIG. 2 is a schematic diagram and flow chart of an alternative embodiment of the apparatus 10 of the present invention. This alternative embodiment includes the means 20 for monitoring an user's pulse and for generating the output pulse signal 22. The output pulse signal 22 corresponds to the user's heart rate (e.g., pulse). The output pulse signal 22 is received by the first amplifying means 24. The first amplifying means 24 adds gain to the output pulse signal 22 to produce the amplified pulse signal 26. The amplified pulse signal 26 is received by the trigger means 28. The trigger means 28 provides the trigger signal 30. The trigger signal 30 is communicated to the means 32 for storing rhythm pattern data. The means 32 for storing rhythm pattern data preferably comprises, as discussed above, the chip that has been preprogrammed with a plurality of rhythm pattern data. The chip generates rhythm tracks from the plurality of rhythm pattern data. The means 32 for storing rhythm pattern data may also communicate with the means 34 for selecting. The means 34 for selecting allows the user to select from the preprogrammed rhythm pattern data.

The means 32 for storing rhythm pattern data produces the output signal 36. The output signal 36 comprises sampled trigger commands, which are received by the sampling means 38. The sampling means 38 produces the digital sample information signal 40. This digital sample information signal is received by the Digital-to-Analog Converter (DAC) 42. The Digital-to-Analog Converter (DAC) 42 receives a digital signal and, as is conventionally known, converts the digital signal into the analog signal 44.

The analog signal 44 is received by a musical mixing means 56. The musical mixing means also receives an audio signal 58 from a music playback device 60. The music playback device may include a conventional CD player, a tape player, a music memory chip, or a combination of devices. The musical mixing means 56 combines the analog signal 44 with the audio signal 58. The musical mixing means 56 generates a combined rhythm/pulse/audio signal 62.

The combined rhythm/pulse/audio signal 62 is received by the second amplifying means 46. The second amplifying means 46 adds gain to the combined rhythm/pulse/audio signal 62 to produce an amplified rhythm/pulse/audio signal 64. The second amplifying means 46 may comprise an operational amplifier as is conventionally known. As those skilled in the art readily recognize, the second amplifying means 46 and the musical mixing means 56 may comprise a conventional mixing pre-amplifier.

The amplified rhythm/pulse/audio signal 64 is received by the output device 50. The output device, as discussed above, may be audio headphones or other speaker devices. The amplified rhythm/pulse/audio signal 64, in this embodiment, represents a combined audio and rhythm signal. The triggered, programmed rhythm is still played at the tempo of the user's heart rate, as discussed above, yet the rhythm is mixed with the audio signal. The user can load the CD player, tape player, or other music device with music of a desired tempo. The user can then exercise at a heart rate which matches the tempo of the music. If, for example, the user's pulse rate does not match the music, the user may increase or decrease activity until the user's pulse matches the tempo of the music. The apparatus and/or system of the present invention is, therefore, very advantageous for athletes, aerobics participants, or even cardiac patients who must monitor and maintain cardiac levels.

Figure 3:
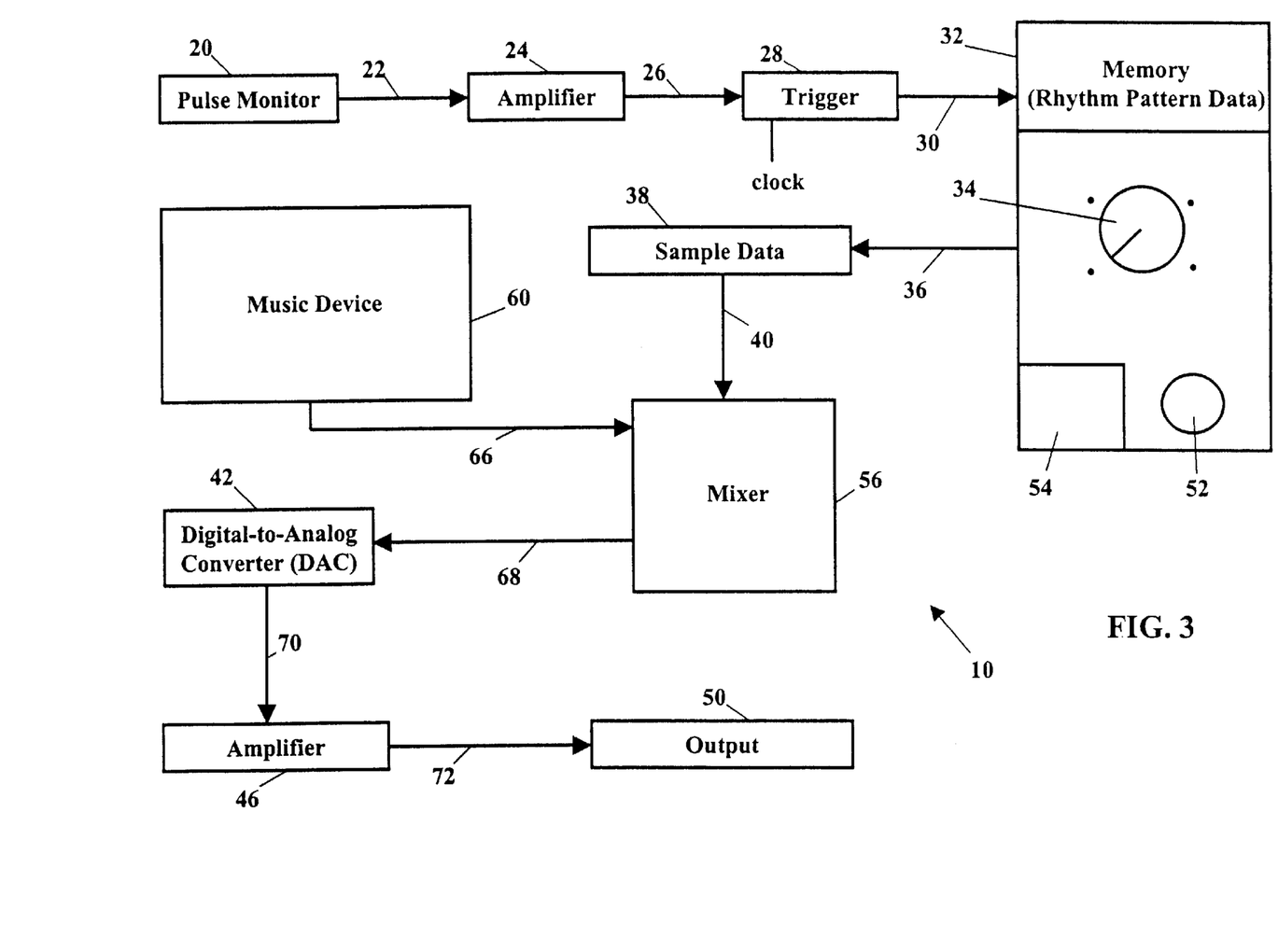
FIG. 3 is a schematic diagram and flowchart of still another alternative embodiment of the present invention.

FIG. 3 is a schematic diagram and flow chart of still another alternative embodiment of the apparatus 10 of the present invention. Although this embodiment is very similar to that shown in FIG. 2, this FIG. 3 embodiment shows an altered configuration for digital music. The sampling means 38, as discussed above, produces the digital sample information signal 40. This digital sample information signal 40, in this embodiment, is not converted to an analog signal. The digital sample information signal 40 is, instead, received by the musical mixing means 56. The musical mixing means also receives a digital audio signal 66 from the music playback device 60. The music playback device may comprise music memory chips, as discussed above, or any other music device supplying digital data (such as Internet downloadable music files). Because the audio signal 66, in this embodiment, is digital, the musical mixing means digitally combines the digital sample information signal 40 and the digital audio signal 66. The musical mixing means generates a digital rhythm/pulse/audio signal 68.

This digital rhythm/pulse/audio signal 68 is received by the Digital-to-Analog Converter (DAC) 42. The Digital-to-Analog Converter (DAC) 42 produces an analog signal 70. The analog signal 70, as discussed above with reference to FIGS. 1 and 2, is received by the second amplifying means 46, and an amplified analog signal 72 is received by the output device 50.

Figure 4:
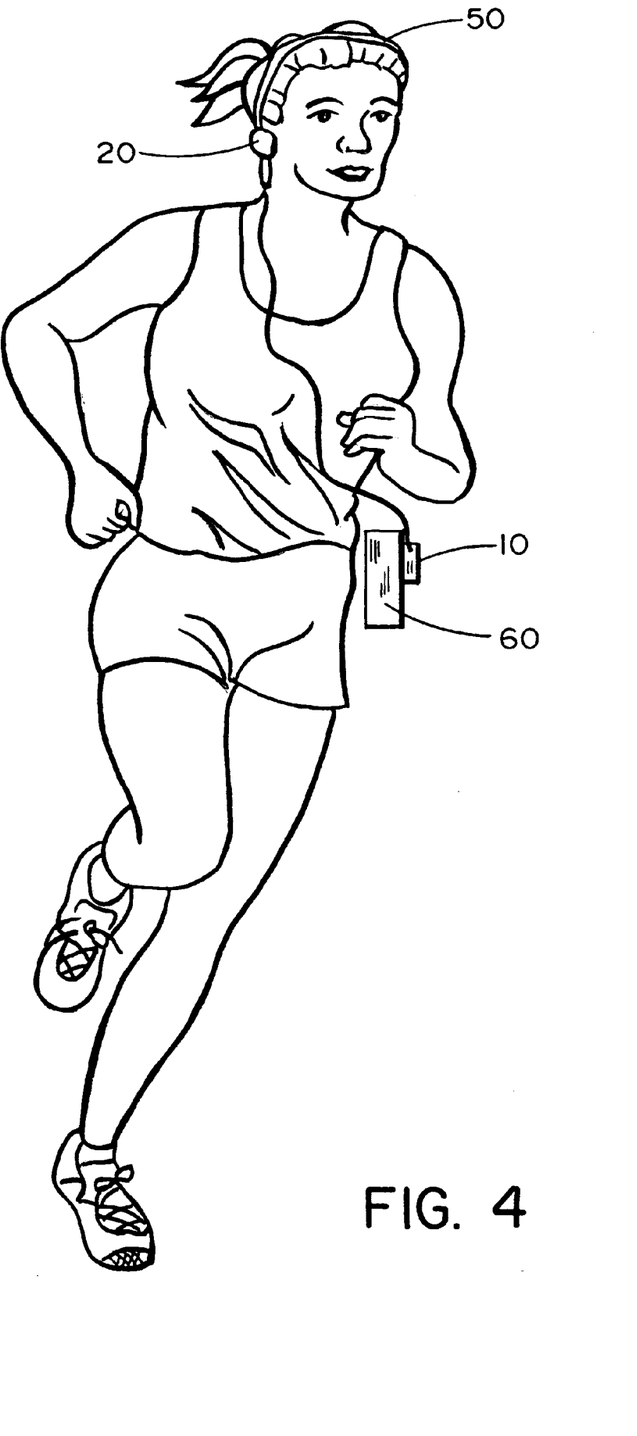
FIG. 4 depicts an individual utilizing a system of the present invention.

FIG. 4 depicts an individual utilizing a system of the present invention. As FIG. 4 shows, the system may include the apparatus of the present invention 10, the pulse monitoring means 20, the output device 50 (shown as headphones), and a portable CD or cassette player 60 all in electrical communication with one another.

Figure 5:
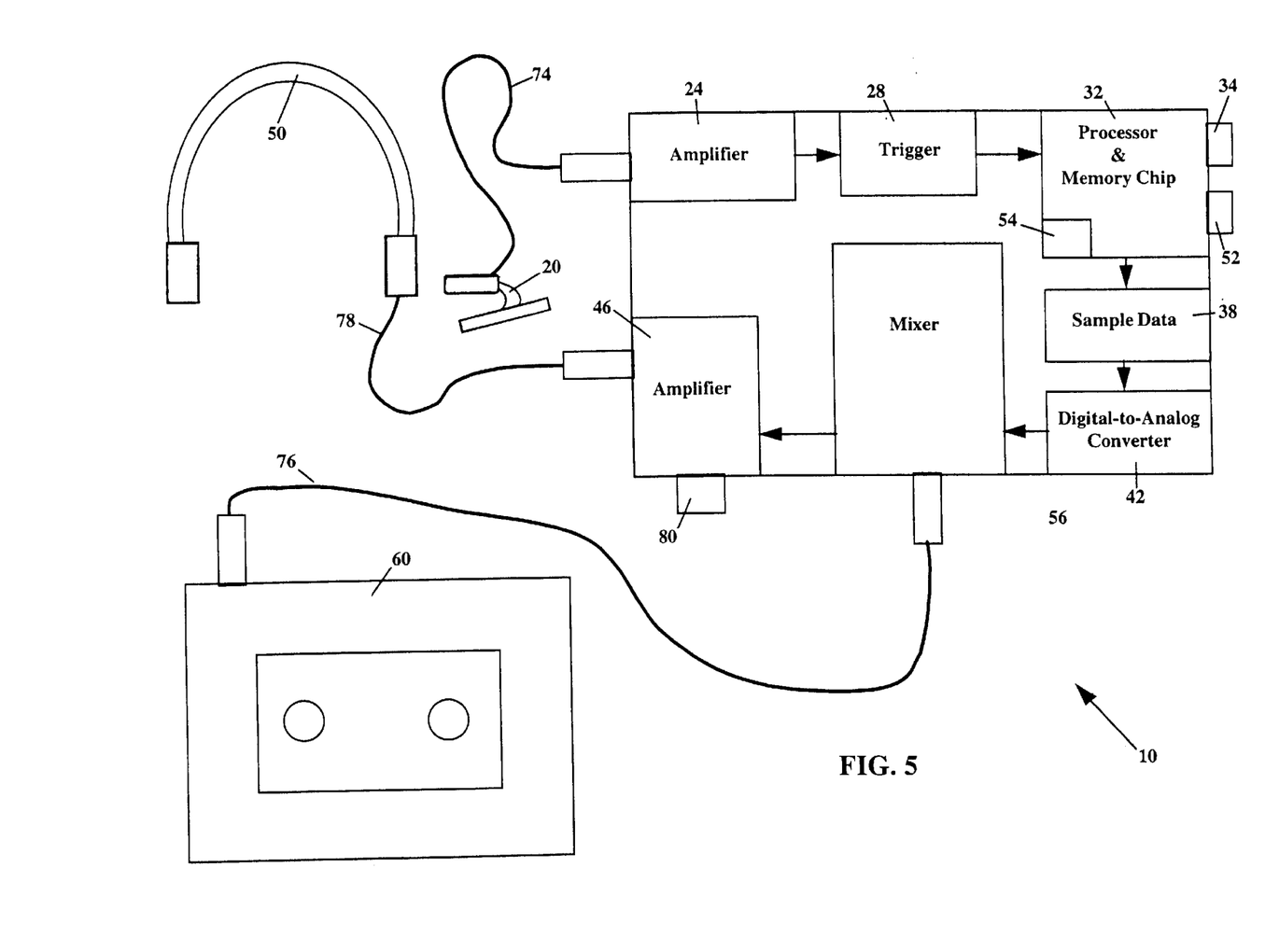
FIG. 5 depicts an apparatus of the present invention as an integrated, stand alone unit.

FIG. 5 depicts the apparatus 10 of the present invention as an integrated unit. The apparatus 10 is shown enlarged for clarity. The means 20 for monitoring a user's pulse is shown as an ear lobe clip. The output pulse signal generated by the ear lobe clip is delivered to the apparatus 10 by a first wire 74. The apparatus 10 is also shown linked to the external music playback device 60 (shown as a cassette player) by a second wire 76. The second wire 76 attaches to the apparatus 10 and the second wire plugs into an output jack receptacle of the music playback device 60. The second wire 76 transmits the music signal (shown as reference numeral 58 in FIG. 2 and reference numeral 66 in FIG. 3) to the apparatus 10. This music signal will be mixed with the rhythm triggered by the user's pulse, as received through the means for monitoring a user's pulse 20. The combined rhythm/pulse/audio signal (shown as reference numeral 48 in FIG. 2 and reference numeral 72 in FIG. 3) is sent to the output device 50 (again shown as headphones) through a third wire 78. A volume control 80 allows the user to select a desired output device volume.

The music used in combination with this invention may comprise a type of non-rhythmic music. The music may comprise electronic sounds or strings, or voices sustaining chords that slowly change into pleasing textures. The monitored music will combine with the rhythm based on the user's heartbeat originating from the apparatus and make it possible for the user to listen to pleasing music with a tempo and rhythm corresponding to the user's heartbeat.

Figure 6:
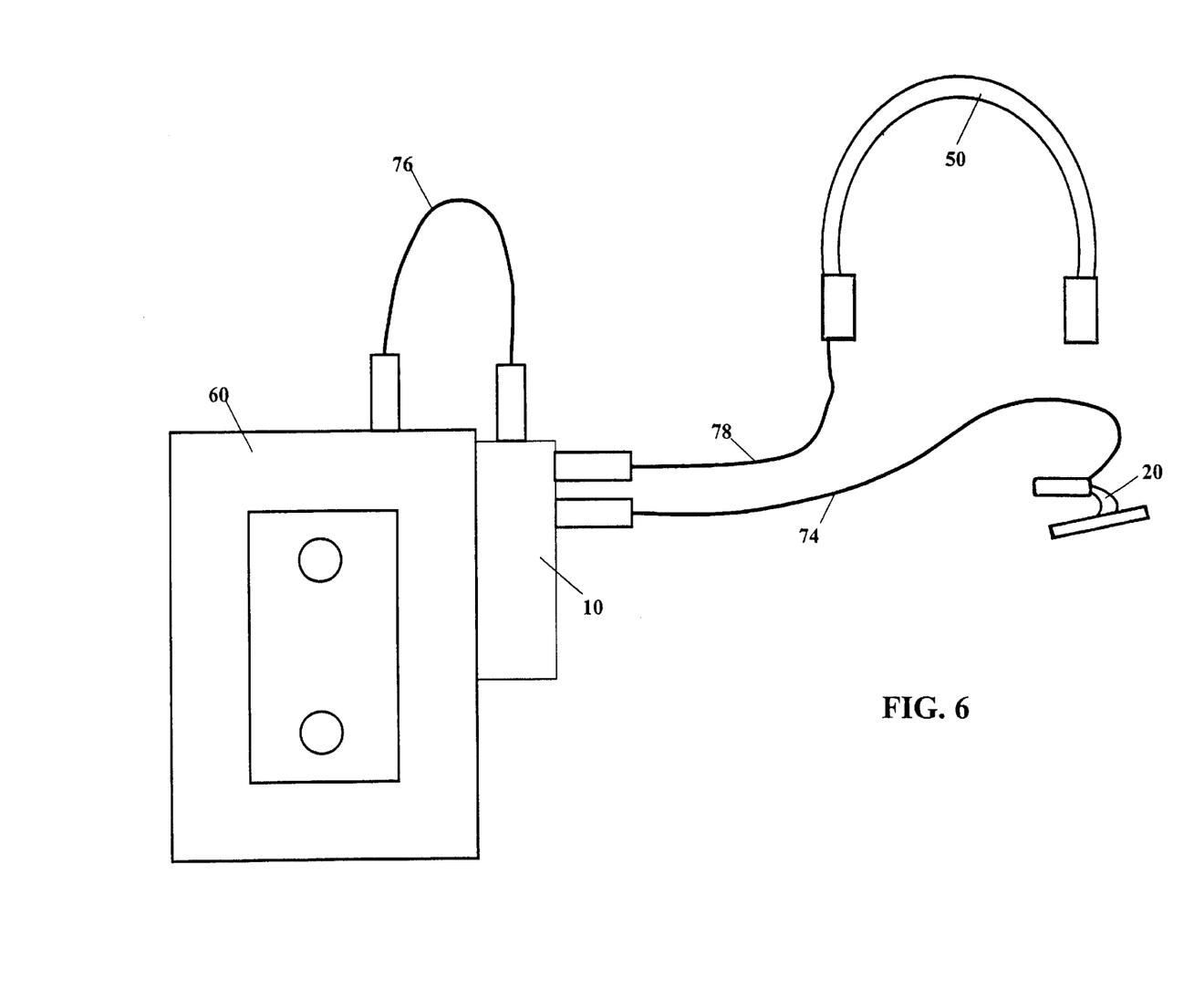
FIG. 6 is a schematic diagram of another embodiment of the apparatus of the present invention.

FIG. 6 also depicts the apparatus 10 of the present invention as an integrated unit. The apparatus 10 is shown, however, in a smaller embodiment for attachment to a conventional music playback device 60 (shown as a cassette tape player).

Figure 7:
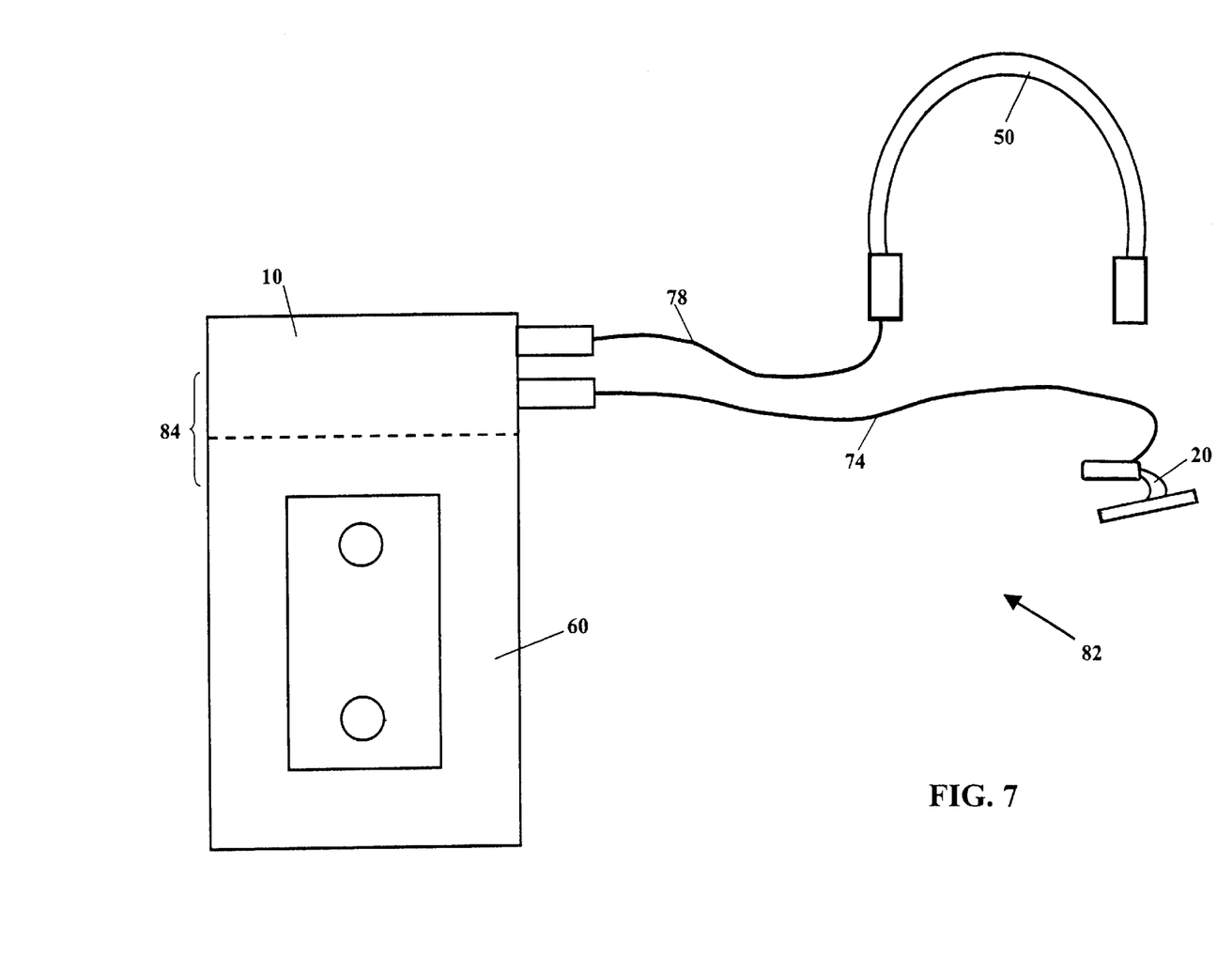
FIG. 7 is a schematic diagram depicting a musical listening device incorporating the apparatus of the present invention.

FIG. 7 is a schematic diagram of a system 82 including the apparatus 10 of the present invention. As those skilled in the art will recognize, the apparatus 10 may be combined with the music playback device 60 to produce a musical listening apparatus 84. The apparatus 10 is advantageously designed as an integral, internal component of the musical listening apparatus.

While the present invention has been described with respect to various features, aspects, and embodiments, those skilled and unskilled in the art will recognize the invention is not so limited. Other variations, modifications, and alternative embodiments may be made without departing from the spirit and scope of the present invention.

What is claimed is:

1. An apparatus for linking a rhythm track with a heartbeat of a user, the apparatus comprising:

means for monitoring the heartbeat of the user, the means for monitoring producing a pulse signal, the pulse signal corresponding to the heartbeat of the user;

means for storing rhythm pattern data;

means for receiving the pulse signal and for receiving the rhythm pattern data;

means for combining the pulse signal with the rhythm pattern data and for generating a linked rhythm and pulse output signal; and means for outputting the linked rhythm and pulse output signal.

2. An apparatus according to claim 1, wherein the means for storing rhythm pattern data includes a plurality of rhythm pattern data.

3. An apparatus according to claim 2, wherein the apparatus further comprises means for selecting one of the plurality of rhythm pattern data, such that the selected rhythm pattern data is combined with the pulse signal.

4. An apparatus according to claim 1, wherein the apparatus further comprises means for alerting the user when a desired pulse rate is achieved and/or exceeded.

5. An apparatus for combining rhythm tracks, a heartbeat of a user, and an audio signal, the apparatus comprising:

means for monitoring a heartbeat of a user, the means for monitoring producing a pulse signal, the pulse signal corresponding to the heartbeat of the user;

means for storing rhythm pattern data;

means for receiving the pulse signal and for receiving the rhythm pattern data;

means for combining the pulse signal with the rhythm pattern data and for generating a linked rhythm/pulse output signal;

means for receiving an audio signal from a music playback device;

musical mixing means for combining the linked rhythm and pulse output signal with the audio signal and for generating a combined rhythm/pulse/audio signal; and means for outputting the combined rhythm/pulse/audio signal.

6. An apparatus according to claim 5, wherein the means for storing rhythm pattern data includes a plurality of rhythm pattern data.

7. An apparatus according to claim 6, wherein the apparatus further comprises means for selecting one of the plurality of rhythm pattern data, such that the selected rhythm pattern data is combined with the pulse signal.

8. An apparatus according to claim 5, wherein the apparatus further comprises means for alerting the user when a desired pulse rate is achieved and/or exceeded.

9. An apparatus for linking a rhythm track with a heartbeat of a user, the apparatus comprising:

a pulse monitor, the pulse monitor producing a pulse signal, the pulse signal corresponding to the heartbeat of the user;

a processor, the processor including memory, the memory storing at least one rhythm pattern data, the processor receiving the pulse signal and the processor receiving the rhythm pattern data, the processor linking the pulse signal with the rhythm pattern data, and the processor producing an output signal; and an output device receiving the output signal from the processor.

10. An apparatus according to claim 9, wherein the apparatus further comprises a switch, the switch allowing the user to select a desired at least one rhythm pattern data, and processor receiving the selected rhythm pattern data.

11. An apparatus according to claim 9, wherein the pulse monitor comprises an electromagnetic sensor.

12. An apparatus according to claim 9, wherein the output device includes at least one audio speaker.

13. An apparatus according to claim 9, wherein the apparatus further comprises alarm circuitry to alert the user when a desired pulse rate is achieved and/or exceeded.

14. A musical listening apparatus for combining rhythm tracks, a heartbeat of a user, and an audio signal, the apparatus comprising:

a music playback device, the music playback device producing an output signal;

a processor, the processor including memory, the memory storing at least one rhythm pattern data, the processor receiving a pulse signal representing the heartbeat of the user, the processor receiving the at least one rhythm pattern data, the processor linking the pulse signal with the rhythm pattern data, and the processor producing an output signal; and a mixer, the mixer combining the output signal from the processor with the output signal from the music playback device.

15. A musical listening apparatus according to claim 14, wherein the music playback device is selected from the group consisting of a CD player, a tape player, a music memory chip, and music files.

16. A musical listening apparatus according to claim 14, wherein the musical listening apparatus further comprises a pulse monitor, the pulse monitor producing the pulse signal that represents the heartbeat of the user.

* * * * *